United States Patent
Rebrovic

(10) Patent No.: US 9,885,002 B2
(45) Date of Patent: Feb. 6, 2018

(54) CARBON DIOXIDE CO-FLUID

(71) Applicant: Emerson Climate Technologies, Inc., Sidney, OH (US)

(72) Inventor: Louis Rebrovic, New Bremen, OH (US)

(73) Assignee: Emerson Climate Technologies, Inc., Sidney, OH (US)

( * ) Notice: Subject to any disclaimer, the term of this patent is extended or adjusted under 35 U.S.C. 154(b) by 0 days.

(21) Appl. No.: 15/496,268

(22) Filed: Apr. 25, 2017

(65) Prior Publication Data

US 2017/0313954 A1    Nov. 2, 2017

Related U.S. Application Data

(60) Provisional application No. 62/329,535, filed on Apr. 29, 2016, provisional application No. 62/329,586, filed on Apr. 29, 2016.

(51) Int. Cl.
  *C09K 5/04* (2006.01)
  *C10M 105/70* (2006.01)
  (Continued)

(52) U.S. Cl.
  CPC ........ *C10M 105/70* (2013.01); *C07D 207/27* (2013.01); *C07D 223/10* (2013.01); *C09K 5/041* (2013.01); *F25B 15/025* (2013.01); *F25B 25/02* (2013.01); *F25B 31/002* (2013.01); *F25B 49/043* (2013.01); *C09K 2205/106* (2013.01); *C10M 2215/22* (2013.01); *C10M 2215/223* (2013.01); *C10N 2240/30* (2013.01); *F25B 2400/23* (2013.01)

(58) Field of Classification Search
  CPC ............ C09K 5/041; C09K 2205/106; C10M 105/68; C10M 2215/22
  See application file for complete search history.

(56) References Cited

U.S. PATENT DOCUMENTS 2,446,988 A    8/1948    Flukes et al.
3,073,843 A    1/1963    Buc
(Continued)

FOREIGN PATENT DOCUMENTS

CN    2667391 Y    12/2004
CN    101329098 A    12/2008
(Continued)

OTHER PUBLICATIONS

International Search Report regarding International Application No. PCT/US2017/029928, dated Jul. 31, 2017.
(Continued)

*Primary Examiner* — John Hardee
(74) *Attorney, Agent, or Firm* — Harness, Dickey & Pierce, P.L.C.

(57) ABSTRACT

A carbon dioxide/co-fluid mixture is provided for use in a refrigeration cycle in which the carbon dioxide is alternately absorbed and desorbed from the co-fluid. Suitable co-fluids are selected from the class of alkoxylated carboxylic amides, wherein the amides are cyclic or non-cyclic. It has been discovered that N-2,5,8,11-tetraoxadodecyl-2-pyrrolidinone and its homologs exhibit an advantageous property of a high rate of desorption at lower temperatures.

24 Claims, 11 Drawing Sheets

(51) Int. Cl.
    *C07D 223/10*  (2006.01)
    *C07D 207/27*  (2006.01)
    *F25B 15/02*   (2006.01)
    *F25B 49/04*   (2006.01)
    *F25B 25/02*   (2006.01)
    *F25B 31/00*   (2006.01)

(56) References Cited

U.S. PATENT DOCUMENTS

| | | | | |
|---|---|---|---|---|
| 3,809,706 | A | * | 5/1974 | Magne et al. ..... C07D 295/185 554/40 |
| 3,846,449 | A | * | 11/1974 | Magne ............... C07D 295/185 544/145 |
| 3,849,321 | A | * | 11/1974 | Magne ............... C07D 295/185 508/249 |
| 3,849,454 | A | * | 11/1974 | Magne et al. ....... C07D 295/18 544/145 |
| 3,853,910 | A | | 12/1974 | Freyermuth et al. |
| 3,873,457 | A | * | 3/1975 | Magne ............... C07D 295/185 508/255 |
| 4,234,435 | A | * | 11/1980 | Meinhardt ............. C10L 1/198 508/192 |
| 4,397,750 | A | * | 8/1983 | Chibnik ............ C07D 207/273 44/346 |
| 4,724,679 | A | | 2/1988 | Radermacher |
| 4,769,454 | A | | 9/1988 | Blank et al. |
| 5,041,622 | A | * | 8/1991 | LeSuer ................ C07C 51/567 549/255 |
| 6,112,547 | A | | 9/2000 | Spauschus et al. |
| 6,415,614 | B1 | | 7/2002 | Greenfield et al. |
| 6,672,091 | B1 | | 1/2004 | Lefor et al. |
| 7,159,407 | B2 | | 1/2007 | Chen |
| 7,765,823 | B2 | | 8/2010 | Shiflett et al. |
| 7,766,994 | B2 | | 8/2010 | Matsuura |
| 7,841,208 | B2 | | 11/2010 | Lefor |
| 8,785,357 | B2 | * | 7/2014 | Mosier ................ C10M 133/40 508/243 |
| 8,852,449 | B2 | | 10/2014 | Carr et al. |
| 2009/0032222 | A1 | | 2/2009 | Birbara et al. |
| 2011/0190180 | A1 | * | 8/2011 | Mosier ................ C10M 129/20 508/267 |

FOREIGN PATENT DOCUMENTS

| | | |
|---|---|---|
| CN | 101486895 A | 7/2009 |
| CN | 101603746 A | 12/2009 |
| CN | 102679614 A | 9/2012 |
| CN | 103977683 A | 8/2014 |
| CN | 103994603 A | 8/2014 |
| JP | S58156194 A | 9/1983 |
| JP | 2000257988 A | 9/2000 |
| JP | 2003075013 A | 3/2003 |
| JP | 2014065923 A | 4/2014 |
| KR | 101154466 B1 | 6/2012 |
| KR | 101343466 B1 | 1/2014 |
| WO | WO-2010008640 A1 | 1/2010 |
| WO | WO-2015034418 A1 | 3/2015 |

OTHER PUBLICATIONS

Written Opinion of the International Searching Authority regarding International Application No. PCT/US2017/029928, dated Jul. 31, 2017.
V. Cuzuel et al. "Amine Degradation in CO2 Capture. 4. Development of complementary analytical strategies for a comprehensive identification of degradation compounds of MEA." International Journal of Greenhouse Gas Control. Sep. 14, 2015. vol. 42, pp. 439-453.
International Search Report regarding International Application No. PCT/US2017/029915, dated Aug. 1, 2017.
Written Opinion of the International Searching Authority regarding International Application No. PCT/US2017/029915, dated Aug. 1, 2017.
Wujek, Scott S. et al., "Experimental and Modeling Improvements to a Co-Fluid Cycle Utilizing Ionic Liquids and Carbon Dioxide", 15$^{th}$ International Refrigeration and Air Conditioning Conference at Purdue, School of Mechanical Engineering, Jul. 14-17, 2014.

* cited by examiner

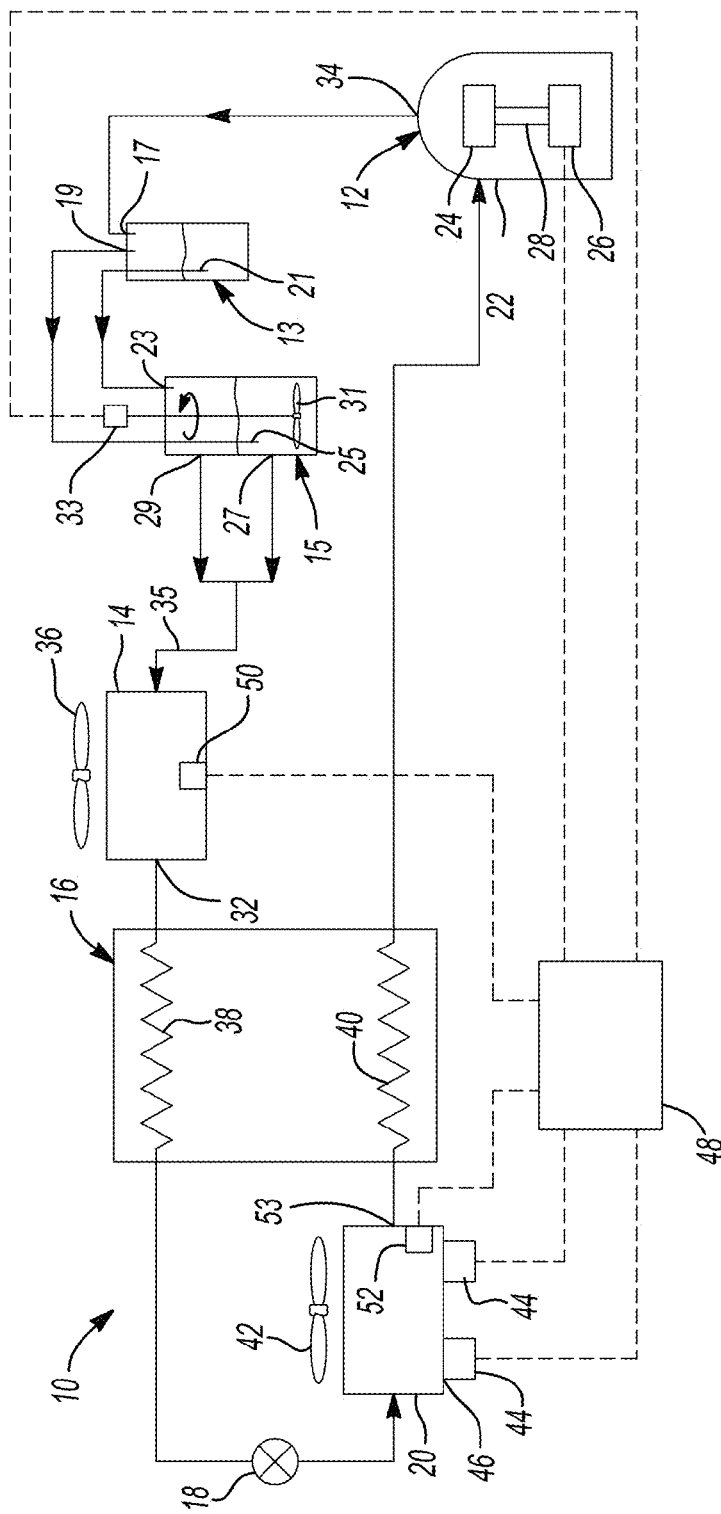
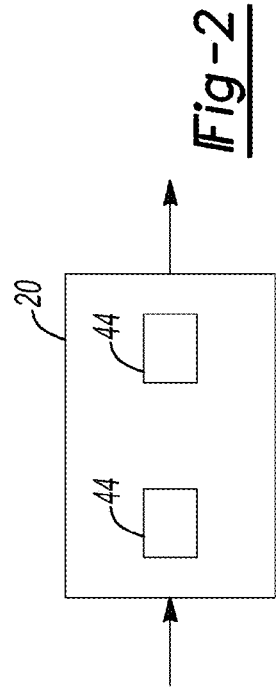

CARBON DIOXIDE CO-FLUID

CROSS-REFERENCE TO RELATED APPLICATIONS

This application claims the benefit of U.S. Provisional Application No. 62/329,535, filed on Apr. 29, 2016, and U.S. Provisional Application No. 62/329,586, filed on Apr. 29, 2016. The entire disclosures of the applications referenced above are incorporated herein by reference.

FIELD

The present disclosure relates to co-fluids for use with carbon dioxide refrigerant in heating, ventilation, air conditioning and refrigeration (HVAC&R) systems.

BACKGROUND

This section provides background information related to the present disclosure which is not necessarily prior art.

Because carbon dioxide (R744) has a low global warming potential (GWP) of only 1 and no ozone-depleting potential at all (ODP of zero), it makes an excellent environmentally friendly refrigerant as compared to hydrofluorocarbons, hydrofluoroolefins, and other less environmentally sound refrigerants. However, the pressures required to liquefy carbon dioxide prove to be too high for use in conventional heating and cooling systems. To avoid high pressures in a refrigeration cycle, carbon dioxide can be used along with a so-called co-fluid or mixture of co-fluids.

In operation of an HVAC&R system using carbon dioxide and a co-fluid, carbon dioxide refrigerant is absorbed into and desorbed out of the co-fluid. For example, carbon dioxide is absorbed and the pressure lowered during compression and flow through a condenser or absorber. Subsequent flow through an expansion device and evaporator requires a desirable release (desorption) of a portion of the carbon dioxide refrigerant.

It has generally been observed that rates of absorption tend to be faster than rates of desorption in co-fluid systems using carbon dioxide as refrigerant. This rate inequality can potentially lead to problems in operating the heating and cooling system. There may not be enough time for proper heat flow to the evaporator needed for cooling. And there could be an accumulation of carbon dioxide in the co-fluid due to the rate difference, causing the system to be inefficient or even inoperable. There is a continuing need for co-fluids that provide a higher rate of desorption to improve operation in cooling systems.

SUMMARY

This section provides a general summary of the disclosure, and is not a comprehensive disclosure of its full scope or all of its features.

A carbon dioxide/co-fluid mixture is provided for use in a refrigeration cycle in which the carbon dioxide is alternately absorbed and desorbed from the co-fluid. The mixture includes from 50% to 99% by weight co-fluid and 1% to 50% by weight carbon dioxide. Suitable co-fluids are selected from the class of alkoxylated carboxylic amides, wherein the amides are cyclic or non-cyclic. It has been discovered that N-2,5,8,11-tetraoxadodecyl-2-pyrrolidinone and its homologs exhibit an advantageous property of a high rate of desorption at lower temperatures.

Pumps or compressors containing the co-fluid as a lubricant are provided for use in a system that includes in sequence a compressor, an absorber (or resorber), an expansion device (or expander), and a desorber. A method of operating a refrigeration system involves circulating the co-fluid and refrigerant around such a system.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a schematic representation of a climate-control system according to the principles of the present disclosure;

FIG. 2 is a schematic representation of an exemplary desorber that can be incorporated into the system of FIG. 1;

Figure 6:
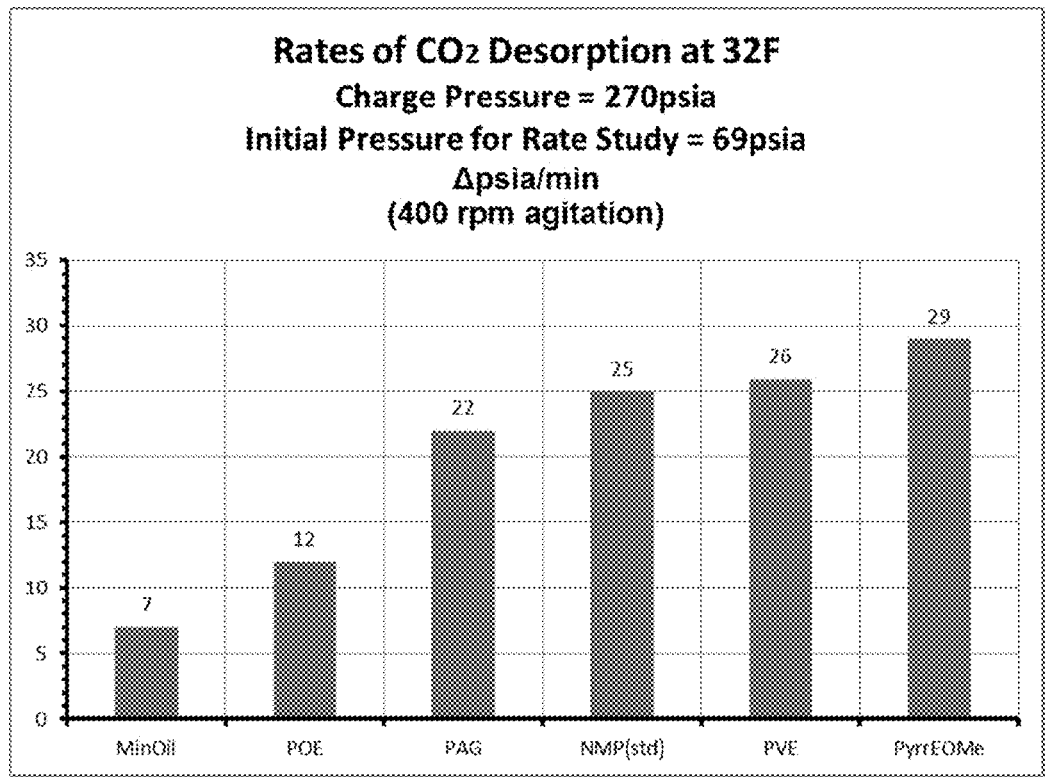
Figure 12:
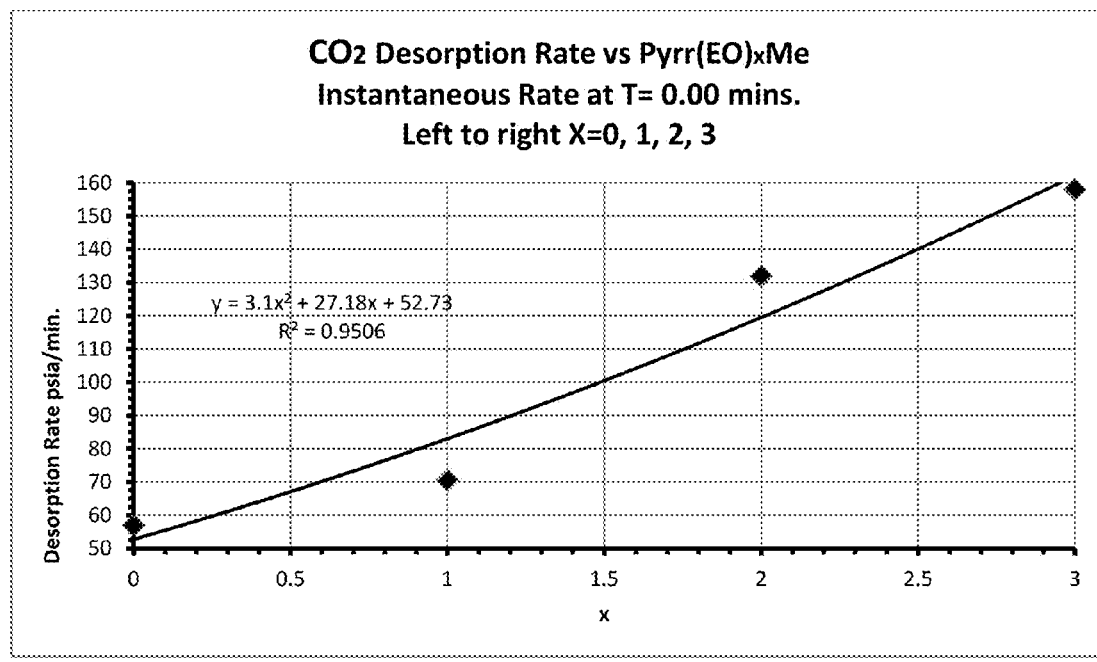

FIG. 6 compares desorption rates among lubricants;

FIGS. 7-11 show comparative desorption rates of co-fluids;

FIG. 12 illustrates carbon dioxide desorption of co-fluids; and

Figure 13:
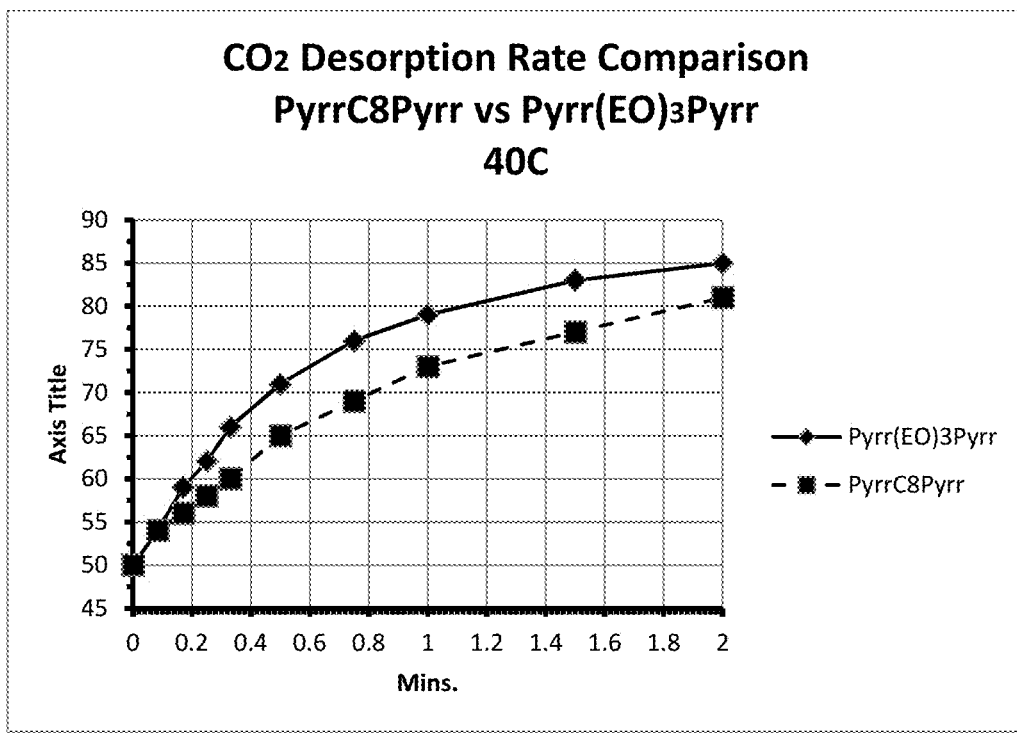

FIG. 13 compares desorption rates to those of co-fluids.

Corresponding reference numerals indicate corresponding parts throughout the several views of the drawings.

DETAILED DESCRIPTION

Example embodiments will now be described more fully with reference to the accompanying drawings.

Co-fluids are provided for use in co-fluid systems where carbon dioxide is used as refrigerant. The co-fluid is an absorbent capable of absorbing and desorbing the carbon dioxide refrigerant. Use of the co-fluids eliminates the need for high system pressures otherwise required to change the phase of the refrigerant carbon dioxide.

Co-fluids are selected from those with the following generic formulae:

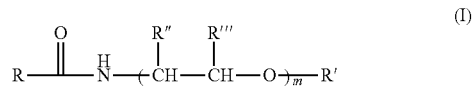

(I)

where m is 1 to 10; R is alkyl, alkenyl, or aryl with 1 to 26 carbon atoms; R' is H or optionally substituted $C_{1-6}$ alkyl; R" is H, methyl, or ethyl; R'" is H, methyl, or ethyl; and at least one of R" and R'" is H;

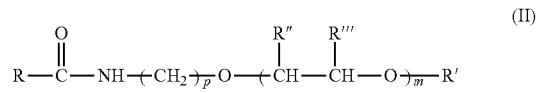

(II)

where m is 1 to 10; p is 1 to 3; R is alkyl, alkenyl, or aryl with 1 to 26 carbon atoms; R' is H or optionally substituted $C_{1-6}$ alkyl; R" is H, methyl, or ethyl; R''' is H, methyl, or ethyl; and at least one of R" and R''' is H;

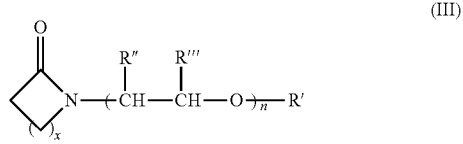

(III)

where x is 1 to 4; n is 1 to 10; R' is H or optionally substituted $C_{1-6}$ alkyl-; R" is H, methyl, or ethyl; R''' is H, methyl, or ethyl; and at least one of R" and R''' is H;

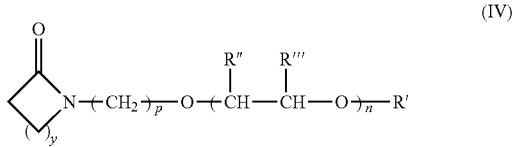

(IV)

where y is 1 to 4; n is 1 to 10; p is 1 to 3; R' is H or optionally substituted $C_{1-6}$ alkyl; R" is H, methyl, or ethyl; R''' is H, methyl, or ethyl; and at least one of R" and R''' is H;

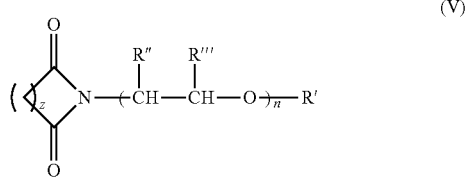

(V)

where z is 1 to 4; n is 1 to 10; R' is H or optionally substituted $C_{1-6}$ alkyl; R" is H, methyl, or ethyl; R''' is H, methyl, or ethyl; and at least one of R" and R''' is H;

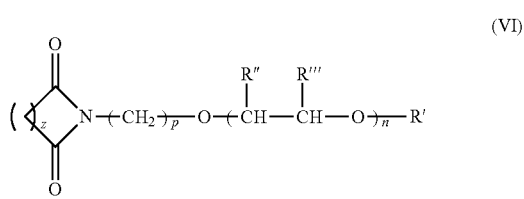

(VI)

where z is 1 to 4; n is 1 to 10; p is 1 to 3; R' is H or optionally substituted $C_{1-6}$ alkyl; R" is H, methyl, or ethyl; R''' is H, methyl, or ethyl; and at least one of R" and R''' is H.

Although the invention is not to be limited by any scientific hypothesis or theory of operation, the compounds of formulae (I)-(VI) share chemical features that are believed to contribute to their general usefulness as co-fluids for use with carbon dioxide refrigerant. It is believed that the carboxylic amide (cyclic or open chain) and the polyoxyalkylene moiety combine to provide compositions that desorb carbon dioxide at a high rate, a rate that is higher than homologous compounds without those features, even though the homologous compounds are considered part of the described invention to the extent they have not yet been disclosed as co-fluids. Generally speaking, species with high desorption rates are preferred as co-fluids in carbon dioxide refrigeration systems, because of the operational advantages expected to flow from having high desorption.

The compounds of formulae (I)-(VI) are characterized by a "side chain" that has a polyoxyalkylene structure denoted by the repeat units of m or n in the formulae. If both of R" and R''' are hydrogen (H), the chain is polyoxyethylene; if one of them is methyl (the other being H), the chain is polyoxypropylene; if one of them is ethyl, the chain is polyoxybutylene. Because the repeat units m and n range from 1 to 10, it is also possible to provide so-called heteric polyoxyalkylene chains containing a combination of polyoxyethylene, polyoxypropylene, and polyoxybutylene. That is to say, the formulae should be interpreted as permitting up to 10 repeat units, where each repeat unit is independently based on ethylene-, propylene-, or butylene oxide.

The non-cyclic amide "alkoxylates" of formulae (I) and (II) are based on carboxylic amides with at least two and up to 27 carbon atoms (since R has 1 to 26 carbon atoms). The nature of the R group (size, level of branching, presence or not of unsaturation) is expected to affect the equivalent weight of and the viscosity of the co-fluid. These are design factors than can be taken into account.

In all formulae, the terminal hydroxyl of the polyoxyalkylene chain is in the alternative capped with an alkyl group (preferably methyl for ease of synthesis) that is optionally substituted. Although part of the invention, the hydroxyl compounds (R'=H) are less preferred in some embodiments because the hydroxyl could contribute to undesirable reactivity, high viscosity, or even corrosion. Capping takes the hydroxyl group out of play. Substitutions on R' are allowed to the extent they do not spoil the operation of the compound as a co-fluid. In a particular embodiment, the alkyl group R' is substituted with a carboxylic amide group as shown in the description below and in the examples. Thus, R' in any of the above can be $C_{1-6}$ alkyl substituted with alkylcarbamido or alkenylcarbamido, represented by the following structures where R is alkyl or alkenyl:

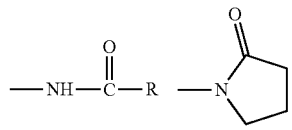

The compounds of formulae (I)-(VI) are formally alkoxylates of the carboxylic amide or -imide shown. The compounds of (I), (III), and (V) can be synthesized by direct alkoxylation of the amide/imide starting group, because the amide/imide group is reactive and can open the oxirane ring of the corresponding alkylene oxides. The compounds of (II), (IV), and (VI) on the other hand, can be made by alkoxylating the free hydroxyl group of a starting material that contains an alkylol moiety attached to the amide or imide. Depending on whether p in the formulae is 1, 2, or 3, the group is a methylol, ethylol, or propylol group.

Compounds with n (or m) from 1 to 10 can be made by reacting the starting material with n or m equivalents of oxide and reacting to a polydisperse mixture containing an average of n oxide units per amide group. Alternatively, they can be synthesized with a goal of producing a molecular weight distribution where the peak is at a species with n oxide units. Various fractions can be physically separated to provide other distributions of alkoxylation.

But especially for the lower molecular weight compounds, it can be simpler not to form the compounds by alkoxylation, but instead by reacting a pre-formed monodisperse compound containing n repeat units with the reactive amide nitrogen (or with the hydroxyl of an alkylol group added to the amide, for example by reaction with formaldehyde). This is illustrated by reacting a starting material N-methylolpyrrolidone (N-hydroxymethyl-2-pyrrolidone) with triethylene glycol monomethyl ether in a conventional Williamson ether synthesis.

In various embodiments, the co-fluids of formulae (I)-(VI) are further characterized by one or any combination of the following: the parameters x and y have a value of either 2 or 4; the parameter z has a value of 2 (meaning the structure is based on a succinimide derivative); the variables n and m are 1 to 4; R' is methyl; R'' and R''' are both H; R' is $C_{1-3}$ alkyl substituted with alkylcarbamido. Particular embodiments include the following:

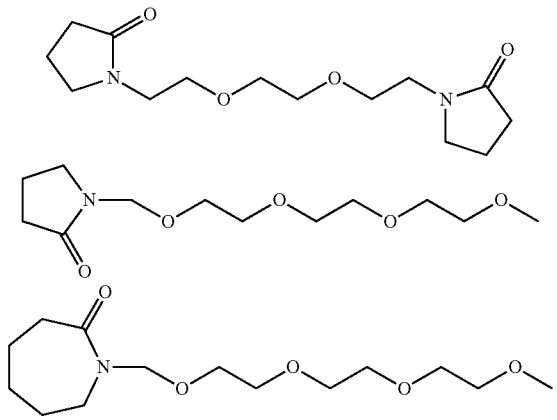

In operation, the co-fluid acts as lubricant as well a carrier fluid for the refrigerant carbon dioxide. A compressor for use in the cooling circuits described herein contains any of the described co-fluids as a lubricant.

In operation, the co-fluids absorb (resorb) and desorb refrigerant carbon dioxide as they circulate around a refrigeration or cooling circuit. At various points in the circuit, a cooling composition comprises from 50% to 99% by weight co-fluid and 1% to 50% by weight carbon dioxide.

Preferred co-fluids have the chemical structures disclosed herein. In various embodiments, performance also relies on a co-fluid having advantageous physical properties as well. Naturally, preferred co-fluids readily absorb and desorb carbon dioxide used as refrigerant. An instantaneous rate (rate essentially at time zero) as well as amount desorbed at 1 minute and at 2 minutes are measured. The results can be used to screen potential candidates.

The co-fluid also needs to have suitable viscosity. In various embodiments, viscosity is in the range of 1 to 50 centistokes (cSt); 1 to 20 cSt; 3 to 20 cSt; 5 to 20 cSt; 1 to 10 cSt; 3 to 10 cSt. Some good candidates have a viscosity of fairly close to 10 cSt. The viscosity is advantageously in a range of 5 to 15 cSt, 8 to 12 cSt, or 9 to 11 cSt, in various embodiments. Too high a viscosity and fluid flow around the cooling circuit can be impeded. If the viscosity is too low, there could be leakage past seals in the system. A non-limiting illustration of use of the co-fluids follows.

Use of the Co Fluids in Refrigeration Methods

A representative refrigeration cycle based on carbon dioxide as refrigerant ("vapor") operates as follows. A combination of vapor and liquid (co-fluid) is compressed in a compressor, raising the pressure and forcing some of the vapor into the liquid phase. Heat is rejected in a resorber (absorber) downstream of the compressor. This cools the mixture and causes more of the vapor to be absorbed. The remaining $CO_2$ vapor and co-fluid are further cooled in an internal heat exchanger. The cool, fully liquefied mixture is then passed through an expansion device, decreasing the pressure, dropping the temperature further, and releasing some of the $CO_2$ into the vapor phase. Heat is extracted from the refrigerated space into a desorber as the temperature of the mixture rises and further $CO_2$ escapes from the liquid phase. Finally, the fluids are further warmed in an internal heat exchanger, completing the cycle.

Binary-Cycle Climate-Control System

With reference to FIG. 1, a binary-cycle climate-control system 10 is provided that may include a compressor 12, a liquid-vapor separator 13, an agitation vessel (e.g., a stirring and/or shaking vessel) 15, an absorber (or resorber) 14, an internal heat exchanger 16, an expansion device 18, and a desorber 20. The compressor 12 can be any suitable type of compressor, such as a scroll, rotary or reciprocating compressor, for example. The compressor 12 may include a shell 22, a compression mechanism 24 disposed within the shell 22, and a motor 26 (e.g., a fixed-speed or variable-speed motor) that drives the compression mechanism 24 via a crankshaft 28. The compressor 12 can be a fixed-capacity or variable-capacity compressor. The compressor 12 may compress a mixture of a refrigerant (e.g., carbon dioxide, hydrofluorocarbons, ammonia, bromide, etc.) and a co-fluid (e.g., oil, water, polyalkylene glycol, polyol ester, polyvinyl ether, etc.) and circulate the mixture throughout the system 10. The co-fluid may be an absorbent capable of absorbing a refrigerant. Compressing the mixture of refrigerant and co-fluid raises the pressure and temperature of the mixture and causes some refrigerant to be absorbed into the co-fluid.

The liquid-vapor separator 13 may include an inlet 17, a first outlet (e.g., a gas outlet) 19, and a second outlet (e.g., a liquid outlet) 21. The inlet 17 may be fluidly coupled with an outlet 34 of the compressor 12 such that the liquid-vapor separator 13 receives the compressed mixture of refrigerant and co-fluid (e.g., the compressed mixture of refrigerant vapor and liquid co-fluid containing some dissolved refrigerant gas) from the compressor 12. The liquid co-fluid (which may contain some dissolved refrigerant gas) may settle to the bottom of the liquid-vapor separator 13, and the undissolved refrigerant vapor may remain at the top (or rise to the top) of the liquid-vapor separator 13 (i.e., above the surface of the liquid co-fluid). The liquid co-fluid may exit the liquid-vapor separator 13 through the second outlet 21 (which may be located below the surface of the liquid in the separator 13), and the refrigerant vapor may exit the liquid-vapor separator 13 through the first outlet 19 (which may be located above the surface of the liquid in the separator 13).

The agitation vessel 15 may include a first inlet 23, a second inlet 25, a first outlet 27, a second outlet 29, and an agitator 31. The first inlet 23 may be disposed at or generally near a top end of the vessel 15 and may be fluidly coupled with the second outlet 21 of the separator 13 such that liquid co-fluid from the separator 13 enters the vessel 15 through the first inlet 23. The liquid co-fluid entering the separator 13 through the first inlet 23 may fall to the bottom of the vessel 15. The second inlet 25 may be below the surface of the liquid co-fluid in the vessel 15 and may be fluidly coupled with the first outlet 19 of the separator 13 such that refrigerant vapor from the separator 13 enters the vessel 15 through the second inlet 25. In this manner, the refrigerant vapor enters the vessel 15 below the surface of the liquid co-fluid, which causes some of the refrigerant vapor entering the vessel 15 to be absorbed (or dissolved) into the liquid co-fluid.

The agitator 31 can be or include an impeller (e.g., one or rotating paddles or blades) and/or a shaker, for example, disposed below the surface of the liquid co-fluid in the vessel 15. The agitator 31 may be driven by a motor 33 and may stir or agitate the liquid co-fluid in the vessel 15 to further promote absorption of the refrigerant vapor into the liquid co-fluid.

The first outlet 27 of the vessel 15 may be disposed below the surface of the liquid co-fluid such that refrigerant vapor exits the vessel 15 through the first outlet 27. The second outlet 29 of the vessel 15 may be disposed above the surface of the liquid co-fluid such that liquid co-fluid (with refrigerant vapor dissolved therein) exits the vessel 15 through the second outlet 29. The first and second outlets 27, 29 may both be in communication with a conduit 35 such that the liquid co-fluid from the first outlet 27 and refrigerant vapor from the second outlet 29 are combined and mix with each other (further promoting absorption of the refrigerant vapor into the liquid co-fluid) in the conduit 35.

The absorber 14 may be a heat exchanger that may be fluidly coupled with the conduit 35 and may receive the compressed mixture of the refrigerant and co-fluid from the conduit 35. In configurations of the system 10 that do not include the separator 13 and vessel 15, the absorber 14 may receive the compressed mixture of the refrigerant and co-fluid directly from the compressor 12. Within the absorber 14, heat from the mixture of the refrigerant and co-fluid may be rejected to air or water for example, or some other medium. In the particular configuration shown in FIG. 1, a fan 36 may force air across the absorber 14 to cool the mixture of the refrigerant and co-fluid within the absorber 14. As the mixture of the refrigerant and co-fluid cools within the absorber 14, more refrigerant is absorbed into the co-fluid.

The internal heat exchanger 16 may include a first coil 38 and a second coil 40. The first and second coils 38, 40 are in a heat transfer relationship with each other. The first coil 38 may be fluidly coupled with the outlet 32 of the absorber 14 such that the mixture of the refrigerant and co-fluid may flow from the outlet 32 of the absorber 14 to the first coil 38. Heat from the mixture of the refrigerant and co-fluid flowing through the first coil 38 may be transferred to the mixture of the refrigerant and co-fluid flowing through the second coil 40. More refrigerant may be absorbed into the co-fluid as the mixture flows through the first coil 38.

The expansion device 18 may be an expansion valve (e.g., a thermal expansion valve or an electronic expansion valve) or a capillary tube, for example. The expansion device 18 may be in fluid communication with the first coil 38 and the desorber 20. That is, the expansion device 18 may receive the mixture of the refrigerant and co-fluid that has exited downstream of the first coil 38 and upstream of the desorber 20. As the mixture of the refrigerant and co-fluid flows through the expansion device 18, the temperature and pressure of the mixture decreases.

The desorber 20 may be a heat exchanger that receives the mixture of the refrigerant and co-fluid from the expansion device 18. Within the desorber 20, the mixture of the refrigerant and co-fluid may absorb heat from air or water, for example. In the particular configuration shown in FIG. 1, a fan 42 may force air from a space (i.e., a room or space to be cooled by the system 10) across the desorber 20 to cool the air. As the mixture of the refrigerant and co-fluid is heated within the desorber 20, refrigerant is desorbed from the co-fluid. From an outlet 53 of the desorber 20, the mixture of refrigerant and co-fluid may flow through the second coil 40 and back to the compressor 12 to complete the cycle.

One or more ultrasonic transducers (i.e., vibration transducers) 44 may be attached to the desorber 20. As shown in FIG. 1, the ultrasonic transducers 44 may be mounted to an exterior surface 46 of the desorber 20. In some configurations, the ultrasonic transducers 44 are disposed inside of the desorber 20 and in contact with the mixture of refrigerant and co-fluid (as shown in FIG. 2). The ultrasonic transducers 44 can be any suitable type of transducer that produces vibrations (e.g., ultrasonic vibrations) in response to receipt of electrical current. For example, the ultrasonic transducers 44 could be piezoelectric transducers, capacitive transducers, or magnetorestrictive transducers. For example, the ultrasonic transducers 44 may have an output frequency in the range of about 20-150 kHz (kilohertz). The ultrasonic transducers 44 may (directly or indirectly) apply or transmit vibration to the mixture of refrigerant and co-fluid flowing through the desorber 20 to increase a rate of desorption of the refrigerant from the co-fluid.

The ultrasonic transducers 44 can have any suitable shape or design. For example, the ultrasonic transducers 44 may have a long and narrow shape, a flat disc shape, etc., and can be flexible or rigid. In configurations in which the ultrasonic transducers 44 are mounted to the exterior surface 46 of the desorber 20, it may be beneficial for the desorber 20 to have a minimal wall thickness at the location at which the ultrasonic transducers 44 are mounted in order to minimize attenuation of the ultrasonic vibration. Furthermore, it may be beneficial to apply the ultrasonic vibration to the mixture of the refrigerant and co-fluid at a location at which the mixture of the refrigerant and co-fluid is static or at a location of reduced or minimal flow rate of the mixture of the refrigerant and co-fluid, because fluids flowing at high rates can be more difficult to excite with ultrasonic energy.

A control module (or controller) 48 may be in communication (e.g., wired or wireless communication) with the ultrasonic transducers 44 and may control operation of the ultrasonic transducers 44. The control module 48 can control the frequency and amplitude of electrical current supplied to the ultrasonic transducers 44 (e.g., electrical current supplied to the ultrasonic transducers 44 by a battery and/or other electrical power source) to control the frequency and amplitude of the vibration that the ultrasonic transducers 44 produce. The control module 48 may also be in communication with and control operation of the motor 26 of the compressor 12, the expansion device 18, the motor 33 of the agitator 31, the fans 36, 42, and/or other components or subsystems.

As described above, applying ultrasonic vibration to the mixture of refrigerant and co-fluid increases the desorption rate. The control module 48 may control operation of the ultrasonic transducers 44 to control the desorption rate. For example, the control module 48 may control the frequency, amplitude, runtime (e.g., pulse-width-modulation cycle time), etc. of the motor 33, fans 36, 42, and/or the ultrasonic transducers 44 such that the desorption rate matches or nearly matches a rate of absorption of the refrigerant into the co-fluid that occurs upstream of the expansion device 18 (e.g., in the absorber 14 and vessel 15).

Without any excitation of the mixture of refrigeration and co-fluid, the absorption rate may be substantially greater than the desorption rate. The absorption rate may vary depending on a variety of operating parameters of the system 10 (e.g., pressure, compressor capacity, fan speed, thermal load on the system 10, type of refrigerant, type of co-fluid, etc.). In some configurations, a first sensor 50 and a second sensor 52 may be in communication with the control module 48 and may measure parameters that are indicative of absorption rate and desorption rate. For example, the first sensor 50 can be a pressure or temperature sensor that measures the pressure or temperature of the mixture of refrigerant and co-fluid within the absorber 14, and the second sensor 52 can be a pressure or temperature sensor that measures the pressure or temperature of the mixture of refrigerant and co-fluid within the desorber 20. The pressures and/or temperatures measured by the sensors 50, 52 may be indicative of absorption rate and desorption rate.

The sensors 50, 52 may communicate the pressure or temperature data to the control module 48, and the control module 48 may determine a concentration of refrigerant in the co-fluid based on the pressure or temperature data (e.g., using a lookup table or equations). The control module 48 can include an internal clock (or be in communication with an external clock) and can determine the absorption rate and desorption rate based on changes in the concentration of refrigerant in the co-fluid over a period of time. The control module 48 may control operation of the ultrasonic transducers 44 based on the absorption rate and/or the desorption rate. The control module 48 may also control operation of the compressor 12, the fans 36, 42 and/or the expansion device 18 based on the absorption and/or desorption rates and/or to control the absorption and/or desorption rates. In some configurations, the control module 48 may control the ultrasonic transducers 44 based on data from additional or alternative sensors and/or additional or alternative operating parameters.

Because the absorption rate of many refrigerants into many co-fluids is significantly faster than the desorption rate, the rate of desorption may substantially limit the capacity of the system 10. Applying ultrasonic energy (e.g., via the ultrasonic transducers 44) to the mixture of refrigerant and co-fluid unexpectedly solves the problem of slow desorption rates. It can be shown that desorption rates may increase by about 100%-900% (depending on the refrigerant type and co-fluid type) by exciting the mixture of refrigerant and co-fluid with ultrasonic energy (e.g., using one or more ultrasonic transducers 44) as compared to stirring the mixture with a propeller at 400 revolutions per minute. This increase in the desorption rate surpassed reasonable expectations of success.

Figure 3:
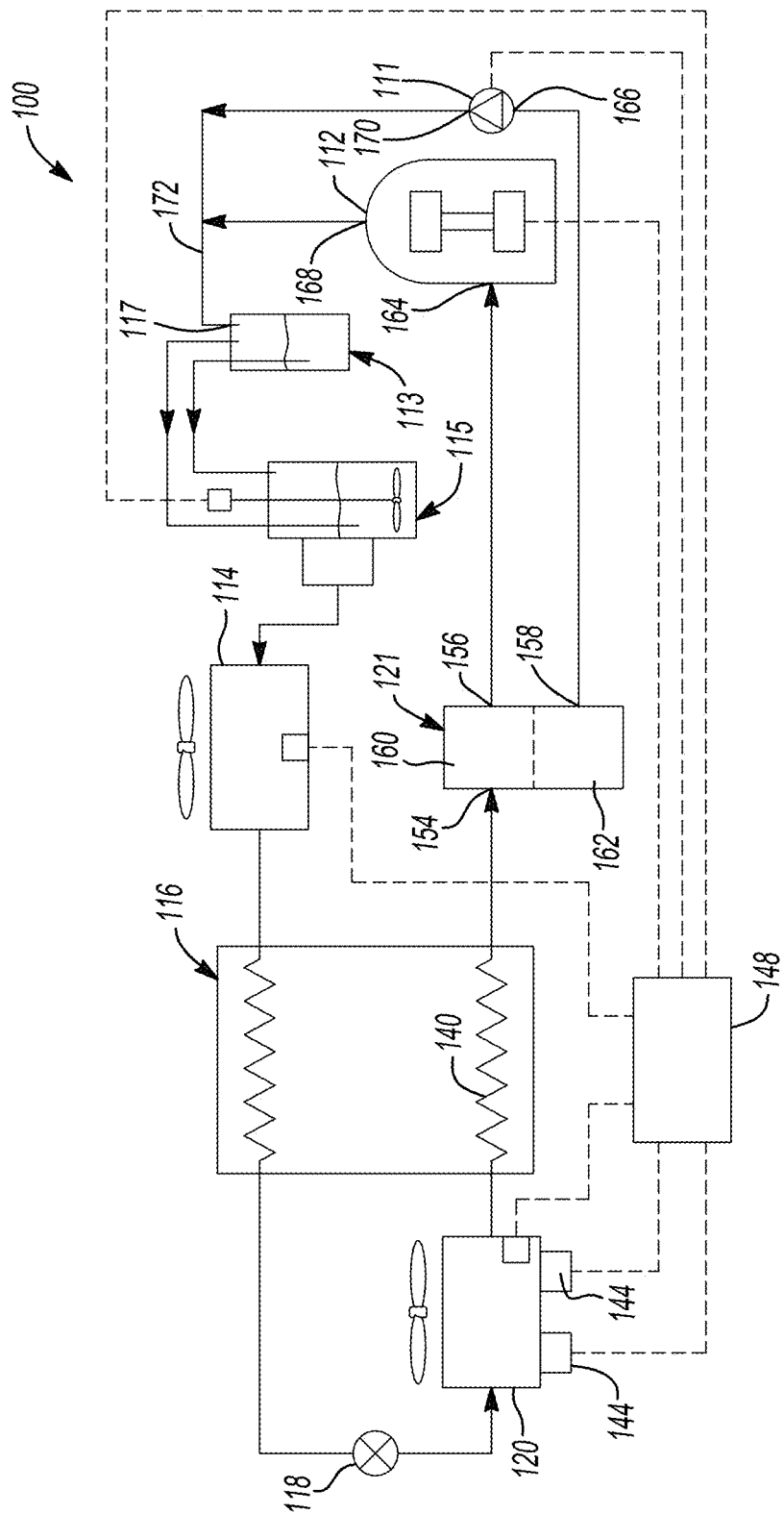
FIG. 3 is a schematic representation of another climate-control system according to the principles of the present disclosure.

Referring now to FIG. 3, another binary-cycle climate-control system 100 is provided that may include a compressor 112, a pump 111, a liquid-vapor separator 113, an agitation vessel (e.g., a stirring and/or shaking vessel) 115, an absorber 114, an internal heat exchanger 116, an expansion device 118, a desorber 120, a receiver 121, one or more ultrasonic transducers 144 and a control module 148. The structure and function of the compressor 112, liquid-vapor separator 113, agitation vessel 115, absorber 114, internal heat exchanger 116, expansion device 118, desorber 120, ultrasonic transducers 144 and control module 148 may be similar or identical to that of the compressor 12, liquid-vapor separator 13, agitation vessel 15, absorber 14, internal heat exchanger 16, expansion device 18, desorber 20, ultrasonic transducers 44 and control module 48 described above (apart from any exceptions described below). Therefore, similar features may not be described again in detail.

The receiver 121 may be fluidly coupled with the internal heat exchanger 116 (e.g., a second coil 140 of the internal heat exchanger 116), the compressor 112, and the pump 111. The receiver 121 may include an inlet 154, a refrigerant outlet 156, and a co-fluid outlet 158. The inlet 154 may receive the mixture of refrigerant and co-fluid from the second coil 140. Inside of the receiver 121, gaseous refrigerant may be separated from liquid co-fluid. That is, the co-fluid accumulates in a lower portion 162 of the receiver 121, and the refrigerant may accumulate in an upper portion 160 of the receiver 121. The refrigerant may exit the receiver 121 through the refrigerant outlet 156, and the co-fluid may exit the receiver 121 through the co-fluid outlet 158. The refrigerant outlet 156 may be fluidly coupled with a suction fitting 164 of the compressor 112 such that refrigerant is drawn into the compressor 112 for compression therein. The co-fluid outlet 158 may be fluidly coupled with an inlet 166 of the pump 111 so that the co-fluid is drawn into the pump 111. Outlets 168, 170 of the compressor 112 and pump 111, respectively, are fluidly coupled with an inlet 117 of the separator 113 via a conduit 172 or with an inlet of the absorber 114 such that refrigerant discharged from the compressor 112 and co-fluid discharged from the pump 111 can be recombine in the vessel 115, in the absorber 114 and/or in the conduit 172 that feeds the separator 113 or the absorber 114.

Figure 4:
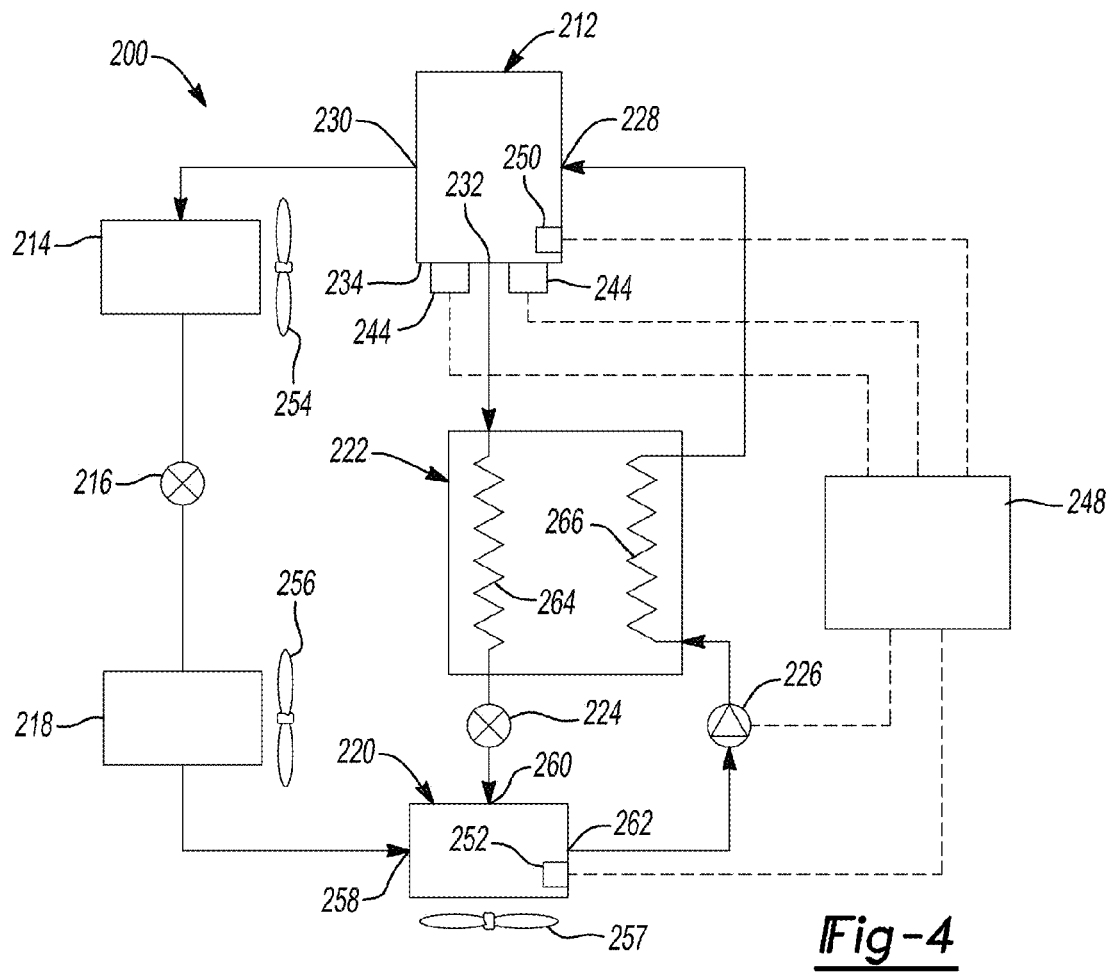
FIG. 4 is a schematic representation of yet another climate-control system according to the principles of the present disclosure.

With reference to FIG. 4, an absorption-cycle climate-control system 200 is provided that may include a vessel 212 (e.g., a generator), a condenser 214, a first expansion device 216, an evaporator 218, an absorber 220, an internal heat exchanger 222, a second expansion device 224, and a pump 226. The vessel 212 may include an inlet 228, a refrigerant outlet 230, and a co-fluid outlet 232. The inlet 228 may receive a mixture of refrigerant and co-fluid (i.e., with the refrigerant absorbed into the co-fluid).

The vessel 212 may be heated by any available heat source (e.g., a burner, boiler or waste heat from another system or machine)(not shown). In some configurations, the vessel 212 may absorb heat from a space to be cooled (e.g., the space to be cooled within a refrigerator, freezer, etc.). As heat is transferred to the mixture of refrigerant and co-fluid within the vessel 212, the vapor refrigerant desorbs from the co-fluid so that the refrigerant can separate from the co-fluid. The refrigerant may exit the vessel 212 through the refrigerant outlet 230, and the co-fluid may exit the vessel 212 through the co-fluid outlet 232.

Figure 5:
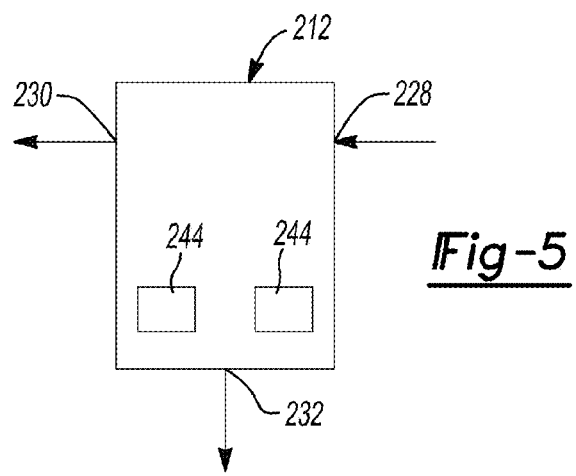
FIG. 5 is a schematic representation of a generator that can be incorporated into the system of FIG. 4.

One or more ultrasonic transducers 244 may be attached to the vessel 212. As shown in FIG. 4, the ultrasonic transducers 244 may be mounted to an exterior surface 234 of the vessel 212. In some configurations, the ultrasonic transducers 244 are disposed inside of the vessel 212 and in contact with the mixture of refrigerant and co-fluid (as shown in FIG. 5). The structure and function of the ultrasonic transducers 244 may be similar or identical to that of the ultrasonic transducers 44 described above. As described above, the ultrasonic transducers 244 produce ultrasonic vibration that is transmitted to the mixture of refrigerant and co-fluid to increase the desorption rate of the refrigerant from the co-fluid. In some configurations, ultrasonic vibration may be used to produce a desired amount of desorption without adding heat from another source. In some configurations, ultrasonic vibration and the addition of heat may further accelerate the desorption rate.

As described above, a control module 248 may be in communication with and control operation of the ultrasonic transducers 244 to increase the desorption rate to a desired level (e.g., to a level matching a rate of absorption). The structure and function of the control module 248 may be similar or identical to that of the control module 48. The control module 248 may be in communication with sensors 250, 252 and may control operation of the ultrasonic transducers 244 based on pressure and/or temperature data received from the sensors 250, 252. The sensor 250 may be disposed within the vessel 212 and may measure a pressure or temperature of the mixture of refrigerant and co-fluid therein. The sensor 252 may be disposed within the absorber 220 and may measure a pressure or temperature of the mixture of refrigerant and co-fluid therein. The control module 248 may also be in communication with and control operation of the pump 226, the expansion devices 216, 224 and/or fans 254, 256, 257.

The condenser 214 is a heat exchanger that receives refrigerant from the refrigerant outlet 230 of the vessel 212. Within the condenser 214, heat from the refrigerant may be rejected to air or water for example, or some other medium. In the particular configuration shown in FIG. 4, the fan 254 may force air across the condenser 214 to cool the refrigerant within the condenser 214.

The expansion devices 216, 224 may be expansion valves (e.g., thermal expansion valves or electronic expansion valves) or capillary tubes, for example. The first expansion device 216 may be in fluid communication with the condenser 214 and the evaporator 218. The evaporator 218 may receive expanded refrigerant from the expansion device 216. Within the evaporator 218, the refrigerant may absorb heat from air or water, for example. In the particular configuration shown in FIG. 4, the fan 256 may force air from a space (i.e., a room or space to be cooled by the system 200) across the evaporator 218 to cool the air.

The absorber 220 may include a refrigerant inlet 258, a co-fluid inlet 260, and an outlet 262. The refrigerant inlet 258 may receive refrigerant from the evaporator 218. The co-fluid inlet 260 may receive co-fluid from the second expansion device 224. Refrigerant may absorb into the co-fluid within the absorber 220. The fan 257 may force air across the absorber 220 to cool the mixture of refrigerant and co-fluid and facilitate absorption.

Like the internal heat exchanger 16, the internal heat exchanger 222 may include a first coil 264 and a second coil 266. The first coil 264 may receive co-fluid from the co-fluid outlet 232 of the vessel 212. The co-fluid may flow from the first coil 264 through the second expansion device 224 and then into the absorber 220 through the co-fluid inlet 260.

The mixture of refrigerant and co-fluid may exit the absorber 220 through the outlet 262, and the pump 226 may pump the mixture through the second coil 266. The mixture of refrigerant and co-fluid flowing through the second coil 266 may absorb heat from the co-fluid flowing through the first coil 264. From the second coil 266, the mixture of refrigerant and co-fluid may flow back into the vessel 212 through the inlet 228.

It will be appreciated that the climate-control systems 10, 100, 200 can be used to perform a cooling function (e.g., refrigeration or air conditioning) or a heating function (e.g., heat pump).

EXAMPLES

Example 1—Comparison to Known Co Fluids

Several commercial lubricants were compared to a co-fluid of the current teachings. MinOil is mineral oil. POE is polyol ester. PAG is polyalkylene glycol. NMP is N-methylpyrrolidone. PVE is polyvinyl ether. Comparison of their desorption rates at 32° F. under the same initial pressure load, initial desorption pressure and agitation rate is plotted in FIG. 6 and compared with N-2,5,8,11-tetraoxadodecyl-2-pyrrolidone (abbreviated: Pyrr(EO)3Me) shown here:

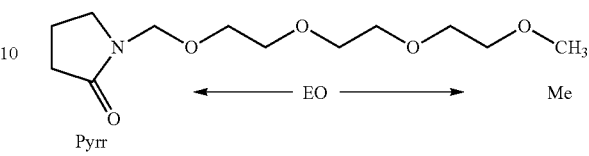

In FIG. 6, each value represents the pressure increase in one minute's time and the values are an average of three trials.

Figure 7:
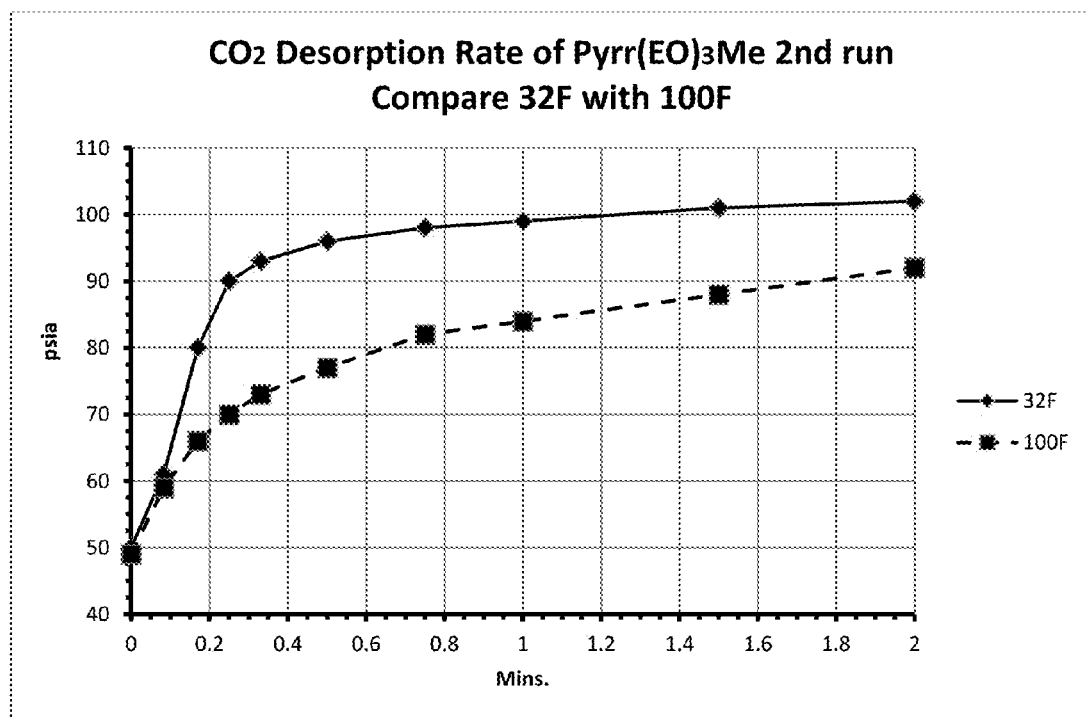

Pyrr(EO)3Me also shows a rate inversion with temperature. Generally, desorption rates are expected to be faster at higher temperatures and slower at lower temperatures. But the plot in FIG. 7 shows that desorption is actually faster at the lower temperature.

Example 2—Comparison of Analog Compounds

A) Comparison of Aliphatic Side Chain and Polyoxyalkylene Side Chain

Figure 8:
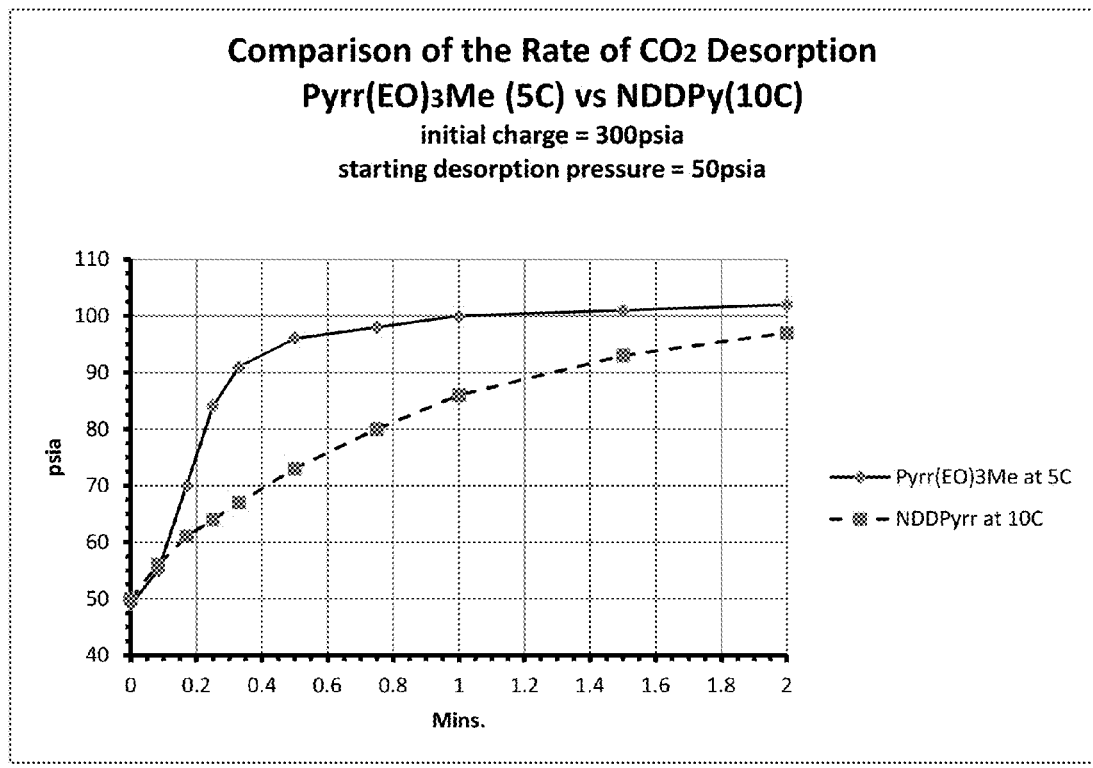

Pyrr(EO)3Me has a 12 atom chain attached to the nitrogen. A saturated analog, N-dodecyl-2-pyrrolidone (Abbreviated: NDDPy), also has a 12-atom chain. They have similar viscosities (NDDPy at 40° C.=9.29 cSt, Pyrr(EO)3Me at 40° C.=9.06 cSt) and are close in molecular weight. NDDPy had to be evaluated at a higher temperature due to it solidifying at 5° C. Pyrr(EO)3Me has a faster desorption rate, as shown in FIG. 8.

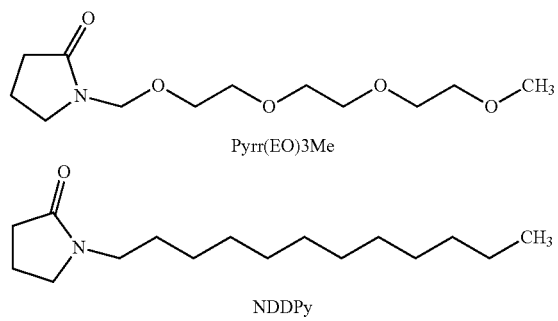

B) Comparison of Carboxylic Amide to Carboxylic Ester

Figure 9:
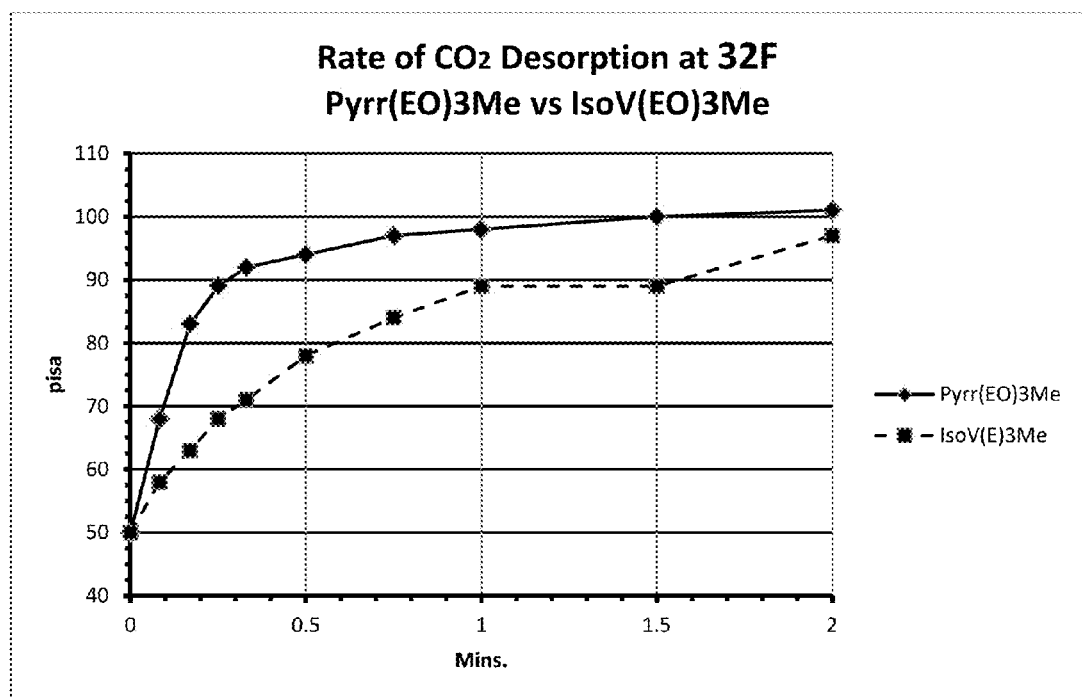

Pyrr(EO3Me) was compared to a corresponding ester compound IsoV(EO)3Me. Although the comparison ester had a lower viscosity than Pyrr(EO)3Me (which would provide a faster desorption rate, all things equal), the Pyrr(EO)3Me had a faster desorption rate. Data are shown in FIG. 9.

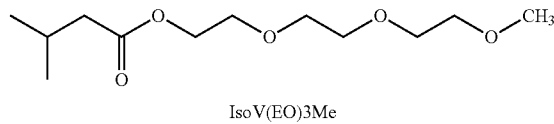

-continued

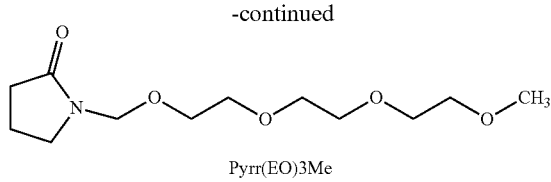

Pyrr(EO)3Me

C) Comparison to a Compound without the Cyclic Carboxylic Amide

Figure 10:
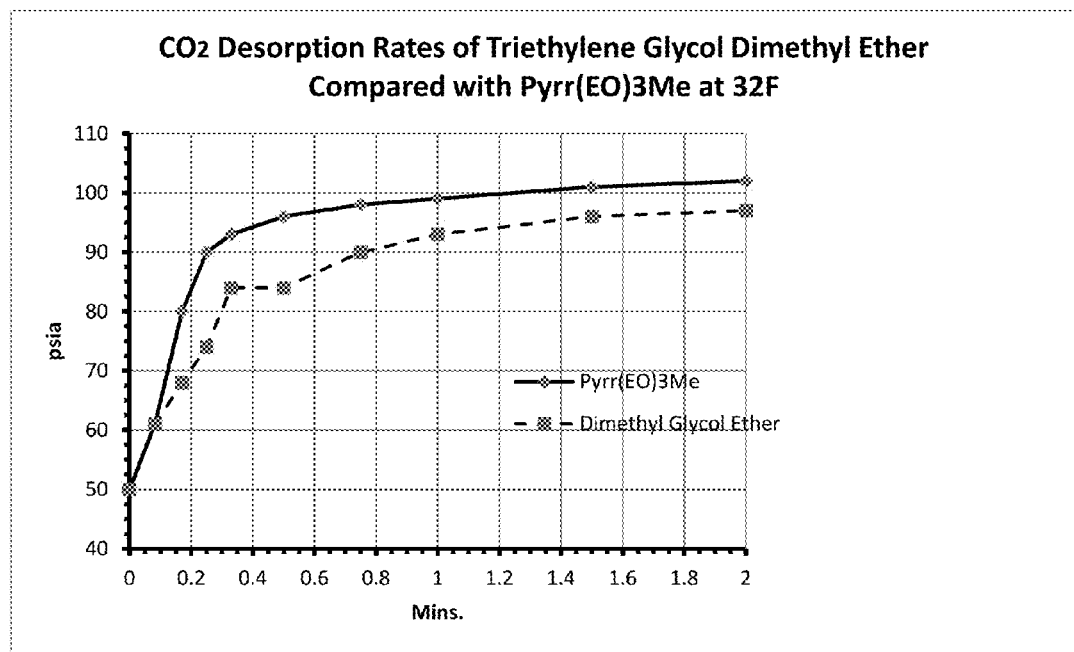
Figure 11:
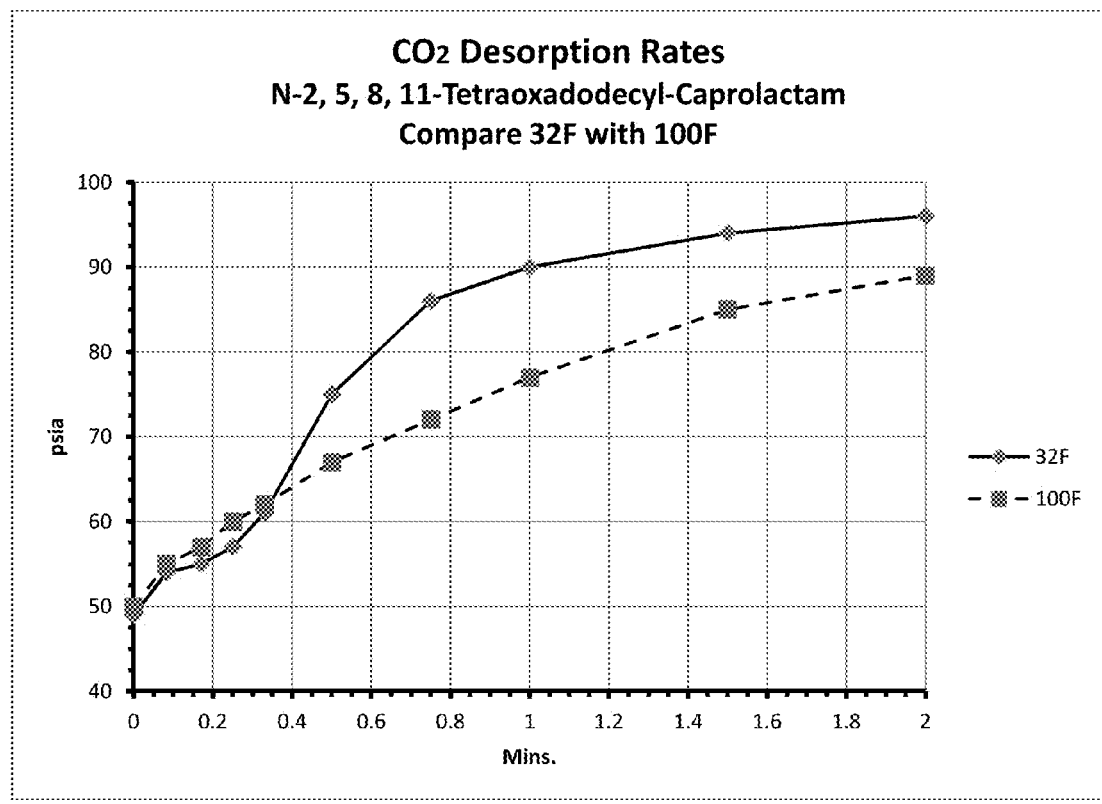

Pyrr(EO)3Me was also compared with triethylene glycol dimethyl ether to show that a low viscosity, low molecular weight polyalkylene glycol would not have the same or better desorption rates. Data are shown in FIG. 10, demonstrating Pyrr(EO)3Me has a faster desorption rate. The "dimethyl glycol ether" of FIG. 10 is triethylene glycol dimethyl ether.

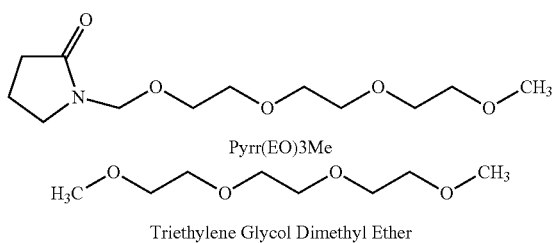

Pyrr(EO)3Me

Triethylene Glycol Dimethyl Ether

D) N-2,5,8,11-Tetraoxadodecyl-Caprolactam Shows the Same Temperature Rate Inversion as Pyrr(EO)3Me.

N-2,5,8,11-Tetraoxadodecyl-Caprolactam has a 7-membered lactam ring rather than the five-membered ring on Pyrr(EO)3Me. It shows a temperature rate inversion, with the data shown in FIG. 11. The analog's structure is:

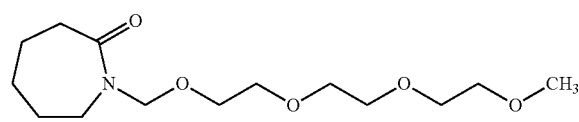 [SMILES: COCCOCCOCCOCN1CCCCCC1=O]

E) Effect of Ethylene Oxide Chain Length on the Rate of Carbon Dioxide Desorption.

The graph in FIG. 12 shows instantaneous rates (rates at time zero) of desorption for a series of compounds with no, 1, 2, or 3 ethylene oxides added to N-hydroxymethyl-2-pyrrolidone, as shown here:

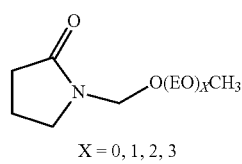

X = 0, 1, 2, 3

F) Desorption Rates of Eight Atom Chain Co-Fluids Double Capped with 2-Pyrrolidone Rings.

The following two compounds were compared at 40° C. This temperature was chosen due to solidification of one of the compounds at 0° C.

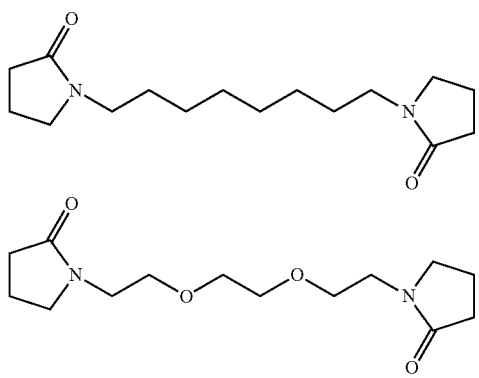

As with the single pyrrolidone capped material (methyl cap at the other end), the compound having both ethylene oxide and pyrrolidone functions desorbs carbon dioxide faster under comparable conditions. This can be seen in the graph in FIG. 13.

Example 3—Synthesis of Co Fluids

Preparation of N-Hydroxymethyl-2-Pyrrolidone (This preparation is a slight modification of U.S. Pat. No. 3,073,843)

To a 250 mL two necked round bottom flask, equipped with a thermometer, magnetic stirrer, and reflux condenser, was added 53.3 g (0.63 moles) 2-pyrrolidone, 19.1 g (0.64 moles) paraformaldehyde, and 0.2 g KOH all at once. The mixture was stirred and heated to 80-90° C. for ~2.5 hours. Afterwards, 100 mL of hot toluene was added. The solution was then filtered and allowed to cool to room temperature. The resulting crystals were filtered and washed with cold toluene to give 64.5 g (89% yield) of 2-hydroxymethyl-2-pyrrolidone. H NMR and FTIR confirmed the structure.

Preparation of N-Hydroxymethyl-2-Caprolactam (This preparation is essentially that of U.S. Pat. No. 4,769,454.)

To a 500 mL round bottom flask equipped with a magnetic stirrer, thermometer, and reflux condenser was added 113.2 g (1.00 mole) of caprolactam, The caprolactam was heated to liquid at which time 31 g (1.0 mole) of paraformaldehyde and 0.7 g of $K_2CO_3$ were added at once. A slight exotherm raised the temperature to 97° C., however the reaction mixture was maintained between 70° C. and 95° C. for 2.5 hours. Afterwards, a seed crystal was added at 57° C. and the mixture held at 50° C. for 18 hours. White crystals resulted with a small amount of liquid. The liquid was decanted away from the white crystals to give 138 g (96% yield) of N-hydroxymethyl-2-caprolactam. H NMR and FTIR confirmed the structure.

Synthesis of N-2,5,8,11-Tetraoxadodecyl-2-Pyrrolidone (See U.S. Pat. No. 3,853,910—hereby incorporated by reference—for hydroxymethyl-2-pyrrolidone ethers of alkyl, aryl, alkenyl, groups etc.)

To a 500 mL two-necked round bottom flask equipped with a magnetic stirrer, thermometer, and reflux condenser was added 58 g (0.50 moles) of N-hydroxymethyl-2-pyrrolidone and 246 g (1.5 moles) of triethylene glycol monomethyl ether at once. The mixture was cooled to ca. 10° C. and 21 mL of 12N HCl was added in 5 to 10 minutes while maintaining the temperature around 10° C. during the addition. Afterwards, the mixture was warmed to room temperature and was held at this temperature for 2 hours while stirring. Addition of 40 g of 25% NaOH to the mixture between 15° C. and 25° C., followed by stirring for 0.5 hours produced a mixture of NaCl and product. The salt was filtered off and the mixture subjected to vacuum distillation to remove water (27° C. at 0.12 Torr). More salt precipitated out and the distillation stopped and the salt filtered off. The resultant oil was distilled three times through a 6×¾ inch Vigreux Column under vacuum. The final cut distilled at 156° C. at 0.11 Torr to give 71.6 g (55% yield) of N-2,5,8,11-tetraoxadodecyl-2-pyrrolidone. H NMR and FTIR confirmed the structure.

Synthesis of N-2,5,8,11-Tetraoxadodecyl-Caprolactam

To a 500 mL two necked round bottom flask equipped with a magnetic stirrer, thermometer, and reflux condenser was added 71.6 g (0.50 moles) of N-hydroxymethyl-caprolactam and 246 g (1.5 moles) of triethylene glycol monomethyl ether at once. The mixture was cooled to ca. 4° C. and 21 mL of 12N HCl was added in ca. 15 minutes while maintaining the temperature around 10° C. during the addition. Afterwards, the mixture was warmed to room temperature and was held at this temperature for 2.5 hours while stirring. Addition of 40 g of 25% NaOH to the mixture between 15° C. and 25° C., followed by stirring for 0.5 hours produced a mixture of NaCl and product. The mixture was subjected to rotoevaporation to remove water. The resultant salt was filtered off and the mixture subjected to straight take over vacuum distillation collecting a top cut between 82° C. and 84° C. More salt precipitated out and the distillation stopped and the salt filtered off. The resultant oil was distilled through a 6×¾ inch Vigreux column under vacuum. The main cut distilled between 159° C. and 169° C. at 0.2 Torr to give 80.1 g (55% yield) of N-2,5,8,11-tetraoxadodecyl-2-caprolactam. H NMR and FTIR confirmed the structure.

Synthesis of 1,8-bis-(Pyrrolidon-1-yl)-3,6-dioxaoctane

To a single necked 500 mL round bottom flask was added 134 g (1.56 mole) gamma-Butyrolactone and 109.5 g (0.74 mole) 1,8-diamino-3,6-dioxaoctane at once. The flask was fitted with a magnetic stir bar, H-Trap and a condenser. At the top of the condenser a nitrogen source was attached via a Firestone Valve. A vacuum was pulled while heating the mixture to melt any resultant solids. This was followed by a vacuum then nitrogen purge three times. While under nitrogen, the mixture was heated and after 26 mL of water was collected in the H-Trap, the reaction mixture was cooled and subjected to straight take-over vacuum distillation. The material was distilled twice and the final product cut distilled between 196° C. and 214° C. at 0.11 Torr to give 124 g of product. H NMR and FTIR confirmed the structure.

Synthesis of 1,8-bis-(pyrrolidon-1-yl)octane

To a single necked 500 mL round bottom flask was added 134 g (1.56 mole) gamma-butyrolactone and 106 g (0.74 mole) 1,8-diaminooctane at once. The flask was fitted with a magnetic stir bar, Dean-Stark Trap and a condenser. At the top of the condenser a nitrogen source was attached via a Firestone Valve. A vacuum was pulled while heating the mixture to melt any resultant solids. This was followed by a vacuum then nitrogen purge four times. While under nitrogen, the mixture was heated and after 27 mL of water was collected in the Dean-Stark Trap, the reaction mixture was cooled and subjected to vacuum distillation. The material was distilled twice and the final product cut distilled between 200° C. and 208° C. at 0.2 Torr to give 166 g (81% yield) of product. H NMR and FTIR confirmed the structure.

Synthesis of 3,6,9-trioxadecyl isovalerate

To a 500 mL single necked round bottom flask equipped with a magnetic stir bar and a Dean-Stark Trap was added 53.7 g (0.526 mole) isovaleric Acid, 81.6 g (0.50 mole) triethylene glycol monomethyl ether, 0.3 g p-toluenesulfonic acid and 200 mL of toluene at once. The mixture was heated under reflux till 8.5 mL of water was collected. After cooling to room temperature, the toluene solution was washed with 200 mL of 5% aqueous NaOH, 200 mL of saturated salt solution and dried over sodium sulfate. The mixture was filtered and subjected to rotoevaporation. Straight take-over distillation gave 91.7 g (73% yield). The product cut was at 107° C. and 115° C. at 1.0 Torr. FTIR confirmed the structure.

Example 4—Measuring Carbon Dioxide Desorption Rate

A co-fluid (50 g) is added to a 300 mL Parr reactor and the reactor is evacuated to ca. 0.21 Torr while stirring and at the temperature being studied. The stirring is stopped, and the co-fluid allowed to settle for 1 minute. $CO_2$ is bled in to the reactor at the required pressure, which is 300 psia unless indicated otherwise. The $CO_2$ is introduced as quietly as possible, with minimal co-fluid agitation. Stirring is then started (400 rpms), time is marked 0 minutes and pressure rate recorded. Equilibrium is recorded generally after 15 minutes of stirring. Note that the equilibrium is reached prior to this.

Afterwards the stirring is stopped and the co-fluid allowed to settle for 1 minute. The pressure is then rapidly but "quietly" dropped to 50 psi. Stirring is resumed and the pressure rise (indicating release of $CO_2$ from the co-fluid) is recorded for a period of time. Instantaneous rates are determined by taking measurements for the first 20 seconds and fitting a straight line curve through the data.

All data points represent at least 3 experimental runs.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A compressor containing a lubricant, wherein the lubricant comprises a compound selected from

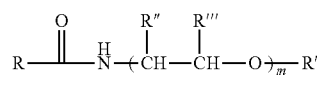 (I)

where m is 1 to 10; R is alkyl, alkenyl, or aryl with 1 to 26 carbon atoms; R' is H or $C_{1-6}$ alkyl; R" is H, methyl, or ethyl; R'" is H, methyl, or ethyl; and at least one R" and R'" is H;

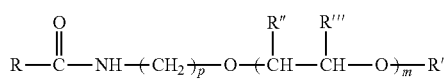 (II)

where m is 1 to 10; R is alkyl, alkenyl, or aryl with 1 to 26 carbon atoms; p is 1 to 3; R' is H or $C_{1-6}$ alkyl; R" is H, methyl, or ethyl; R'" is H, methyl, or ethyl; and at least one R" and R'" is H;

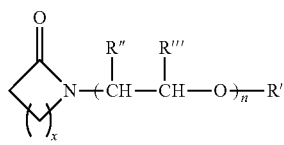 (III)

where x is 1 to 4; n is 1 to 10; R' is H or optionally substituted $C_{1-6}$ alkyl; R" is H, methyl, or ethyl; R'" is H, methyl, or ethyl; and at least one R" and R'" is H;

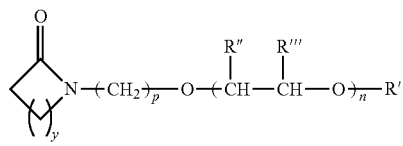 (IV)

where y is 1 to 4; n is 1 to 10; p is 1 to 3; R' is H or $C_{1-6}$ alkyl; R" is H, methyl, or ethyl; R'" is H, methyl, or ethyl; and at least one R" and R'" is H;

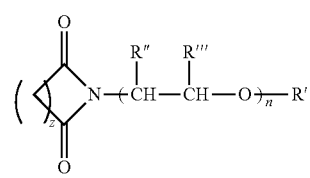 (V)

where z is 1 to 4; n is 1 to 10; R' is H or optionally substituted $C_{1-6}$ alkyl; R" is H, methyl, or ethyl; R'" is H, methyl, or ethyl; and at least one of R" and R'" is H; and

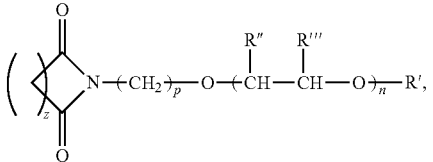 (VI)

where z is 1 to 4; n is 1 to 10; p is 1 to 3; R' is H or optionally substituted $C_{1-6}$ alkyl; R" is H, methyl, or ethyl; R'" is H, methyl, or ethyl; and at least one of R" and R'" is H.

2. The compressor of claim 1, wherein the lubricant comprises a compound of formula

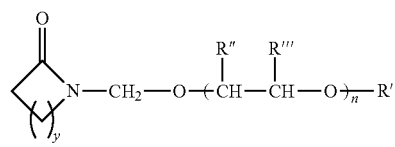

where y is 1 to 4; n is 1 to 10; R' is H or optionally substituted $C_{1-6}$ alkyl; R" is H, methyl, or ethyl; R'" is H, methyl, or ethyl; and at least one R" and R'" is H.

3. The compressor of claim 2, wherein y is 2 or 4.
4. The compressor of claim 2, wherein n is 1 to 4.
5. The compressor of claim 2, wherein R' is methyl.
6. The compressor of claim 2, wherein R" and R'" are H.
7. The compressor of claim 2, wherein y is 2 or 4, n is 3, R' is methyl, and R" and R'" are both H.
8. The compressor of claim 1, wherein the lubricant comprises a compound of formula

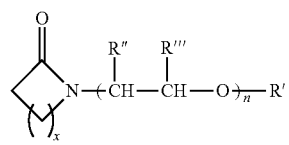

where x is 1 to 4; n is 1 to 10; R' is H or optionally substituted $C_{1-6}$ alkyl; R" is H, methyl, or ethyl; R'" is H, methyl, or ethyl; and at least one R" and R'" is H.

9. The compressor of claim 8, wherein x is 2 or 4.
10. The compressor of claim 8, wherein n is 1 to 4.
11. The compressor of claim 8, wherein R' is methyl or $C_{1-3}$ alkyl substituted with alkylcarbamido.
12. The compressor of claim 8, wherein R" and R'" are H.
13. The compressor of claim 8, wherein x is 2 or 4, n is 3, R' is methyl, and R" and R'" are both H.
14. The compressor of claim 1, wherein the lubricant comprises a compound selected from

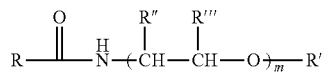

where m is 1 to 10; R is alkyl, alkenyl, or aryl with 1 to 26 carbon atoms; R' is H or optionally substituted $C_{1-6}$ alkyl; R" is H, methyl, or ethyl; R'" is H, methyl, or ethyl; and at least one R" and R'" is H.

15. The compressor of claim 14, wherein R is alkyl.

16. The compressor of claim 14, wherein R' is methyl.

17. The compressor of claim 14, wherein m is 1 to 4.

18. The compressor of claim 14, wherein both R" and R'" are H.

19. The compressor of claim 14, wherein R is alkyl with 7 to 17 carbon atoms.

20. The compressor of claim 14, wherein the lubricant is selected from

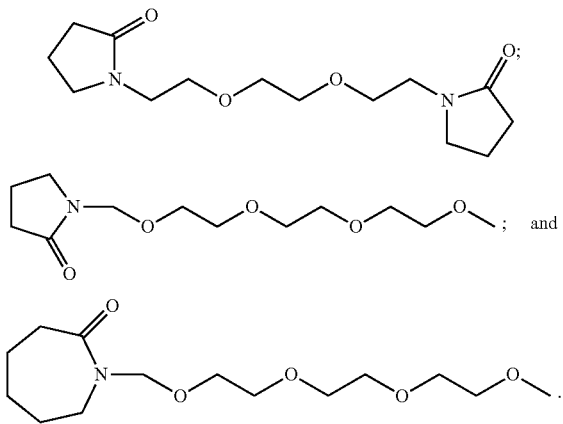

21. The compressor of claim 1, circulating a mixture through a climate control system, wherein the mixture comprises the lubricant and a refrigerant, wherein the refrigerant comprises carbon dioxide.

22. A cooling composition comprising carbon dioxide and a co-fluid, wherein the co-fluid is selected from compounds of formula

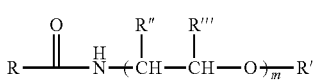

where m is 1 to 10; R is alkyl, alkenyl, or aryl with 1 to 26 carbon atoms; R' is H or $C_{1-6}$ alkyl; R" is H, methyl, or ethyl; R'" is H, methyl, or ethyl; and at least one R" and R'" is H;

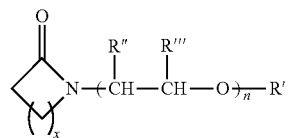

where x is 1 to 4; n is 1 to 10; R' is H or optionally substituted $C_{1-6}$ alkyl; R" is H, methyl, or ethyl; R'" is H, methyl, or ethyl; and at least one R" and R'" is H; and

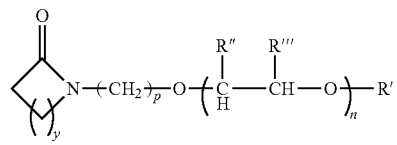

where y is 1 to 4; n is 1 to 10; p is 1 to 3; R' is H or optionally substituted $C_{1-6}$ alkyl; R" is H, methyl, or ethyl; R'" is H, methyl, or ethyl; and at least one R" and R'" is H.

23. The cooling composition of claim 22, wherein the co-fluid is selected from

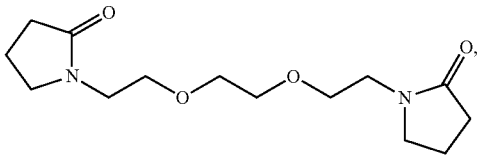

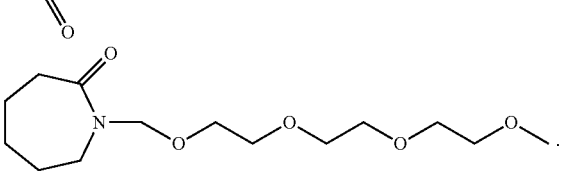

24. A method of operating a refrigeration system comprising pumping the cooling composition according to claim 22 around a circuit containing in sequence a compressor, an absorber, an expander, and a desorber.

* * * * *